United States Patent
Ye et al.

(10) Patent No.: US 10,702,468 B2
(45) Date of Patent: Jul. 7, 2020

(54) TEA MASSAGE OIL, PREPARATION METHOD THEREFOR AND APPLICATION THEREOF

(71) Applicant: SOUTH CHINA UNIVERSITY OF TECHNOLOGY, Guangzhou (CN)

(72) Inventors: Yong Ye, Guangzhou (CN); Qian Yang, Guangzhou (CN)

(73) Assignee: SOUTH CHINA UNIVERSITY OF TECHNOLOGY, Guangzhou (CN)

( * ) Notice: Subject to any disclaimer, the term of this patent is extended or adjusted under 35 U.S.C. 154(b) by 0 days.

(21) Appl. No.: 16/334,364

(22) PCT Filed: Nov. 21, 2017

(86) PCT No.: PCT/CN2017/112103
§ 371 (c)(1),
(2) Date: Mar. 19, 2019

(87) PCT Pub. No.: WO2018/130008
PCT Pub. Date: Jul. 19, 2018

(65) Prior Publication Data
US 2019/0216716 A1     Jul. 18, 2019

(30) Foreign Application Priority Data

Jan. 13, 2017 (CN) .......................... 2017 1 0025804

(51) Int. Cl.
| | | |
|---|---|---|
| *A61K 36/00* | (2006.01) | |
| *A61K 8/92* | (2006.01) | |
| *A61Q 19/00* | (2006.01) | |
| *A61K 8/19* | (2006.01) | |
| *A61Q 17/00* | (2006.01) | |
| *A61N 5/06* | (2006.01) | |

(52) U.S. Cl.
CPC ............... *A61K 8/922* (2013.01); *A61K 8/19* (2013.01); *A61Q 19/00* (2013.01); *A61K 2800/5922* (2013.01); *A61N 2005/0659* (2013.01); *A61Q 17/005* (2013.01)

(58) Field of Classification Search
None
See application file for complete search history.

(56) References Cited

U.S. PATENT DOCUMENTS 10,137,076 B1 * 11/2018 Sica ..................... A61K 8/9789

FOREIGN PATENT DOCUMENTS

| CN | 101268995 | 9/2008 | |
|---|---|---|---|
| CN | 101472483 | 7/2009 | |
| CN | 101491489 | 7/2009 | |
| CN | 101736047 | 6/2010 | |
| CN | 102342331 | 2/2012 | |
| CN | 104490635 | 4/2015 | |
| CN | 106726782 | 5/2017 | |
| WO | WO-2010086716 A1 * | 8/2010 | ............. A61K 8/922 |

* cited by examiner

*Primary Examiner* — Terry A McKelvey
*Assistant Examiner* — Russell G Fiebig
(74) *Attorney, Agent, or Firm* — JMB Davis Ben-David

(57) ABSTRACT

The present invention, belonging to the field of daily skin care products, discloses a tea massage oil, a preparation method therefor and an application thereof. The tea massage oil is prepared from the following raw materials in parts by weight: 40-87 parts of ethyl-esterified tea oil, 5-15 parts of oregano oil, 2-12 parts of *melaleuca alternifolia* oil, 2-10 parts of pumpkin seed oil, 2-10 parts of prickly pear seed oil, 1-10 parts of passion fruit seed oil, and 1-5 parts of nano germanium oxide. The method comprises: evenly mixing the ethyl-esterified tea oil, the oregano oil, the *melaleuca alternifolia* oil, the pumpkin seed oil, the prickly pear seed oil, the passion fruit seed oil, and the nano germanium oxide, so as to obtain the tea massage oil. The tea massage oil can eliminate fatigue, achieve a men's health-care function, remove scars, and achieve a far-infrared skin activating function.

7 Claims, No Drawings

TEA MASSAGE OIL, PREPARATION METHOD THEREFOR AND APPLICATION THEREOF

CROSS-REFERENCE TO RELATED APPLICATIONS

This is the U.S. National Stage of International Patent Application No. PCT/CN2017/112103 filed Nov. 21, 2017, which was published in Chinese under PCT Article 21(2), and which in turn claims the benefit of China Patent Application No. 201710025804.0 filed Jan. 13, 2017.

FIELD OF THE INVENTION

The present invention belongs to the field of skin care products, and particularly relates to a tea massage oil, a preparation method therefor and an application thereof.

BACKGROUND OF THE INVENTION

Massage is a physiotherapy method that stimulates acupuncture points, relaxes muscles, and relieves fatigue and stress. Massage oil is used during massage. The skin oil used to enhance the massage effect usually consists of essential oil and base oil. Essential oil, volatile, is used to stimulate and relax the brain; and base oil is used to dilute essential oil and has nutritional functions.

At present, there are many kinds of massage oils on the market, but most of them are synthetic base oils containing chemical substances or hormones, which are detrimental to human health if used for a long time. Vegetable oil and volatile oil, safe for the human body and the environment, are also widely used as massage oil, but they have unreasonable components and a single effect, and offer no massage oil product for men's health.

*Camellia* oil has the effect of nourishing the skin. Patent Application No. 200810066987.1 and Patent Application No. 201410758075.6 disclose a massage oil using tea seed oil as a basis or component; however, the tea oil is sticky and has poor dispersity, and if it is used directly as a massage base oil or for compatibility, it will be not conducive to the penetration of active ingredients in the massage oil into the skin to activate the skin.

CONTENTS OF THE INVENTION

In order to overcome the shortcomings and deficiencies of the prior art, it is a primary object of the present invention to provide a tea massage oil. The present invention adopts the ethyl-esterified tea oil with good dispersity as the base oil, together with the antibacterial essential oil and the plant nutrient oil, and utilizes the far-infrared effect of the nano germanium to activate the skin, thereby playing a good role in promoting nutrient absorption and protecting the skin, especially suitable for protecting men's health.

Another object of the present invention is to provide a method for preparing the above tea massage oil. The present invention prepares the ethyl-esterified tea oil by an enzymatic method under mild conditions to ensure that the nutrient composition of the tea oil is not destroyed, and exerts the multi-effect health care function of the massage oil through reasonable compatibility.

The objects of the present invention are achieved through the following technical solution:

The tea massage oil is prepared from the following raw materials in parts by weight:

40-87 parts of ethyl-esterified tea oil, 5-15 parts of oregano oil, 2-12 parts of *melaleuca alternifolia* oil, 2-10 parts of pumpkin seed oil, 2-10 parts of prickly pear seed oil, 1-10 parts of passion fruit seed oil, and 1-5 parts of nano germanium oxide. The sum of the parts by weight of each raw material is preferably 100.

The tea massage oil is preferably prepared from the following raw materials in parts by weight:

70 parts of ethyl-esterified tea oil, 10 parts of oregano oil, 5 parts of *melaleuca alternifolia* oil, 5 parts of pumpkin seed oil, 5 parts of prickly pear seed oil, 3 parts of passion fruit seed oil, and 2 parts of nano germanium oxide.

The ethyl-esterified tea oil is prepared by the following method: The tea seed oil is mixed with ethanol to obtain a mixture, and an immobilized lipase is added to the mixture to react at a certain temperature; then centrifugation is performed, and the supernatant is taken and rinsed with a saturated sodium chloride aqueous solution; and then the rinsed supernatant is allowed to stand layering, and the lower layer is removed to obtain the ethyl-esterified tea oil.

The volume ratio of the tea seed oil to ethanol is 1:(1 to 5), the amount of the immobilized lipase is 0.5% to 5% of the mass of the tea seed oil, the reaction temperature is 30° C. to 70° C., and the reaction time is 12-24 h.

The immobilized lipase is one or both of Lipozyme TL IM and Lipozyme 435.

The centrifugal speed is 1000-5000 rpm, and the centrifugal time is 20-60 min; the amount of the saturated sodium chloride aqueous solution is 0.5 to 3 times the mass of the tea seed oil.

The method for preparing the tea massage oil comprises the following step: evenly mixing the ethyl-esterified tea oil, the oregano oil, the *melaleuca alternifolia* oil, the pumpkin seed oil, the prickly pear seed oil, the passion fruit seed oil, and the nano germanium oxide, so as to obtain the tea massage oil. The massage oil has a viscosity of 27-45 mPa·s.

The tea massage oil is used as a fatigue-relieving massage product, a men's health massage product, a scar-removing massage product, and/or a skin-activating massage product. The tea massage oil can eliminate fatigue, achieve a men's health-care function, remove scars, and achieve a far-infrared skin activating function.

Principle: Although having nutritional and antibacterial effects, the tea oil itself has high viscosity, which is not conducive to uniform application; the present invention makes the tea oil into the ethyl-esterified tea oil by a transesterification method, thereby improving the fluidity and comfort of the tea oil. The oregano oil, as a volatile oil of oregano grass, is rich in carvacrol and othymol, and has the functions of reducing fever, dissipating dampness, dispelling summer heat, relieving exterior syndrome, and regulating the flow of qi (vital energy), as well as strong bactericidal and bacteriostatic effects. The *melaleuca alternifolia* oil, mainly containing terpineol, terpinene, etc., has strong antibacterial ability against *staphylococcus aureus*, and is thus an excellent natural antibacterial agent. The pumpkin seed oil, containing plant sterols, amino acids, vitamins, minerals and other biologically active substances, especially high in the content of zinc, magnesium, calcium and phosphorus, is a healthy nutrient oil having prominent men's health-care effects and can prevent benign prostatic hyperplasia. The prickly pear seed oil, mild in nature, has obvious effects on eliminating facial fine lines, pigmentation, stretch marks, scars and acne, and pimples. The passion fruit seed oil, rich in linolenic acid, is easily absorbed by the skin and can prevent the formation of melanin. Germanium oxide, non-toxic, can generate negative ions and emit far infrared rays at body temperature, and has the functions of metabolism and blood circulation promotion, anti-inflammatory and analgesia, and immunity regulation. The nano germanium oxide enhances the affinity and far-infrared effect of germanium oxide on skin; it is used in combination with other raw materials, taking advantage of the nutritional effects of the tea oil, the pumpkin seed oil, the prickly pear seed oil and the passion fruit seed oil as well as the antibacterial effects of the oregano oil and the *melaleuca alternifolia* oil, to form a multifunctional tea massage oil.

The present invention has the following advantages and effects with respect to the prior art:

(1) The components of the massage oil of the present invention, all being natural products without preservatives, artificial flavors and hormones, are not irritating to the skin.

(2) The massage oil of the present invention, using the ethyl-esterified tea oil as the base oil, has low viscosity, good fluidity, and clear and transparent appearance, comforting the skin.

(3) The massage oil of the present invention, by using the nano germanium oxide, can generate negative ions and emit far infrared rays at body temperature to activate skin, improving the therapeutic effect of massage.

(4) Since the components of the massage oil of the present invention, having different functions such as repairing and regenerating, promoting absorption, being antibacterial, reducing inflammation, protecting health and removing scars, are made compatible, the massage oil of the present invention has the synergistic effect of the components and is thus a multifunctional massage oil suitable for men's health care.

DETAILED DESCRIPTION OF THE EMBODIMENTS

The present invention will be further described below in detail with reference to examples, but the embodiments of the present invention are not limited thereto. In the examples, the oregano oil, which is the oregano grass steam distilled oil, is produced by Dingcheng Plant and Spice Co., Ltd. of Shenzhen City; the *melaleuca alternifolia* oil, which is the *melaleuca alternifolia* burgeon steam distilled oil, is produced by Zhongxiang Natural Plant Co., Ltd. of Ji'an City; the pumpkin seed oil, which is the cold-pressed first-grade pumpkin seed oil, is produced by Changbai Gongfang Science and Trade Co., Ltd. of Jilin Province; the prickly pear seed oil, which is the prickly pear seed pressed oil, is produced by Najel Cosmetics Co. of France; the passion fruit seed oil, which is the passion fruit seed pressed oil, is produced by Guoxin Flavor & Fragrance Co., Ltd. of Shenzhen City; and the nano germanium oxide, which is the nano germanium dioxide, is produced by Tianlong Mineral Processing Plant of Linglong County.

EXAMPLE 1

A tea massage oil was prepared from the following raw materials in parts by weight:

70 parts of ethyl-esterified tea oil, 10 parts of oregano oil, 5 parts of *melaleuca alternifolia* oil, 5 parts of pumpkin seed oil, 5 parts of prickly pear seed oil, 3 parts of passion fruit seed oil, and 2 parts of nano germanium oxide.

The preparation method for the tea massage oil comprised the following steps:

(1) Preparation of the ethyl-esterified tea oil: the tea seed oil (*camellia* seed oil) and ethanol were mixed at a volume ratio of 1:3 to obtain a mixture, and the immobilized lipase of Lipozyme TL IM that was 1% by mass of the tea seed oil was added to the mixture, and then the above mixed materials reacted at 40° C. for 20 h; centrifugation was performed at 3000 rpm for 30 min, and then the supernatant was rinsed with a saturated sodium chloride aqueous solution twice as much as the mass of the tea seed oil; then the rinsed supernatant was allowed to stand layering, and the lower layer was removed to obtain the ethyl-esterified tea oil; and (2) evenly mixing the ethyl-esterified tea oil, the oregano oil, the *melaleuca alternifolia* oil, the pumpkin seed oil, the prickly pear seed oil, the passion fruit seed oil, and the nano germanium oxide, so as to obtain the tea massage oil.

The massage oil prepared in this example has a density of 0.938 g/mL and a viscosity of 32 mPa·s, which are only ¼ of the corresponding values of the general vegetable oil; therefore, it is easy to disperse, good in bacteriostatic performance, and stable, having no obvious change after being sealed at room temperature for 18 months.

EXAMPLE 2

A tea massage oil was prepared from the following raw materials in parts by weight:

87 parts of ethyl-esterified tea oil, 5 parts of oregano oil, 2 parts of *melaleuca alternifolia* oil, 2 parts of pumpkin seed oil, 2 parts of prickly pear seed oil, 1 part of passion fruit seed oil, and 1 part of nano germanium oxide.

The preparation method for the tea massage oil comprised the following steps:

(1) Preparation of the ethyl-esterified tea oil: the tea seed oil and ethanol were mixed at a volume ratio of 1:5 to obtain a mixture, and the immobilized lipase of Lipozyme 435 that was 5% by mass of the tea seed oil was added to the mixture, and then the above mixed materials reacted at 30° C. for 24 h; centrifugation was performed at 1000 rpm for 60 min, and then the supernatant was rinsed with a saturated sodium chloride aqueous solution triple as much as the mass of the tea seed oil; then the rinsed supernatant was allowed to stand layering, and the lower layer was removed to obtain the ethyl-esterified tea oil; and (2) evenly mixing the ethyl-esterified tea oil, the oregano oil, the *melaleuca alternifolia* oil, the pumpkin seed oil, the prickly pear seed oil, the passion fruit seed oil, and the nano germanium oxide, so as to obtain the tea massage oil.

The massage oil prepared in this example has a density of 0.925 g/mL and a viscosity of 27 mPa·s, which are only ⅕ of the corresponding values of the general vegetable oil; therefore, it is easy to disperse, good in bacteriostatic performance, and stable, having no obvious change after being sealed at room temperature for 18 months.

EXAMPLE 3

A tea massage oil was prepared from the following raw materials in parts by weight:

40 parts of ethyl-esterified tea oil, 15 parts of oregano oil, 10 parts of *melaleuca alternifolia* oil, 10 parts of pumpkin seed oil, 10 parts of prickly pear seed oil, 10 parts of passion fruit seed oil, and 5 parts of nano germanium oxide.

The preparation method for the tea massage oil comprised the following steps:

(1) Preparation of the ethyl-esterified tea oil: the tea seed oil and ethanol were mixed at a volume ratio of 1:1 to obtain a mixture, and the immobilized lipase of Lipozyme TL IM that was 0.5% by mass of the tea seed oil was added to the mixture, and then the above mixed materials reacted at 70° C. for 12 h; centrifugation was performed at 5000 rpm for 20 min, and then the supernatant was rinsed with a saturated sodium chloride aqueous solution half as much as the mass of the tea seed oil; then the rinsed supernatant was allowed to stand layering, and the lower layer was removed to obtain the ethyl-esterified tea oil; and (2) evenly mixing the ethyl-esterified tea oil, the oregano oil, the *melaleuca alternifolia* oil, the pumpkin seed oil, the prickly pear seed oil, the passion fruit seed oil, and the nano germanium oxide, so as to obtain the tea massage oil.

The massage oil prepared in this example has a density of 0.963 g/mL and a viscosity of 45 mPa·s, which are only ⅓ of the corresponding values of the general vegetable oil; therefore, it is easy to disperse, good in bacteriostatic performance, and stable, having no obvious change after being sealed at room temperature for 18 months.

EXAMPLE 4

A tea massage oil was prepared from the following raw materials in parts by weight:

50 parts of ethyl-esterified tea oil, 8 parts of oregano oil, 6 parts of *melaleuca alternifolia* oil, 6 parts of pumpkin seed oil, 4 parts of prickly pear seed oil, 4 parts of passion fruit seed oil, and 2 parts of nano germanium oxide.

The preparation method for the tea massage oil comprised the following steps:

(1) Preparation of the ethyl-esterified tea oil: the tea seed oil and ethanol were mixed at a volume ratio of 1:2 to obtain a mixture, and the immobilized lipase of Lipozyme 435 that was 2% by mass of the tea seed oil was added to the mixture, and then the above mixed materials reacted at 50° C. for 16 h; centrifugation was performed at 2000 rpm for 30 min, and then the supernatant was rinsed with a saturated sodium chloride aqueous solution twice as much as the mass of the tea seed oil; then the rinsed supernatant was allowed to stand layering, and the lower layer was removed to obtain the ethyl-esterified tea oil; and (2) evenly mixing the ethyl-esterified tea oil, the oregano oil, the *melaleuca alternifolia* oil, the pumpkin seed oil, the prickly pear seed oil, the passion fruit seed oil, and the nano germanium oxide, so as to obtain the tea massage oil.

The massage oil prepared in this example has a density of 0.947 g/mL and a viscosity of 41 mPa·s, which are only ⅓ of the corresponding values of the general vegetable oil; therefore, it is easy to disperse, good in bacteriostatic performance, and stable, having no obvious change after being sealed at room temperature for 18 months.

EXAMPLE 5

A tea massage oil was prepared from the following raw materials in parts by weight:

57 parts of ethyl-esterified tea oil, 12 parts of oregano oil, 8 parts of *melaleuca alternifolia* oil, 8 parts of pumpkin seed oil, 6 parts of prickly pear seed oil, 6 parts of passion fruit seed oil, and 3 parts of nano germanium oxide.

The preparation method for the tea massage oil comprised the following steps:

(1) Preparation of the ethyl-esterified tea oil: the tea seed oil and ethanol were mixed at a volume ratio of 1:4 to obtain a mixture, and the immobilized lipase of Lipozyme 435 that was 4% by mass of the tea seed oil was added to the mixture, and then the above mixed materials reacted at 36° C. for 18 h; centrifugation was performed at 3000 rpm for 40 min, and then the supernatant was rinsed with a saturated sodium chloride aqueous solution triple as much as the mass of the tea seed oil; then the rinsed supernatant was allowed to stand layering, and the lower layer was removed to obtain the ethyl-esterified tea oil; and (2) evenly mixing the ethyl-esterified tea oil, the oregano oil, the *melaleuca alternifolia* oil, the pumpkin seed oil, the prickly pear seed oil, the passion fruit seed oil, and the nano germanium oxide, so as to obtain the tea massage oil.

The massage oil prepared in this example has a density of 0.942 g/mL and a viscosity of 37 mPa·s, which are only ¼ of the corresponding values of the general vegetable oil; therefore, it is easy to disperse, good in bacteriostatic performance, and stable, having no obvious change after being sealed at room temperature for 18 months.

EXAMPLE 6

A tea massage oil was prepared from the following raw materials in parts by weight:

64 parts of ethyl-esterified tea oil, 6 parts of oregano oil, 12 parts of *melaleuca alternifolia* oil, 5 parts of pumpkin seed oil, 4 parts of prickly pear seed oil, 7 parts of passion fruit seed oil, and 2 parts of nano germanium oxide.

The preparation method for the tea massage oil comprised the following steps:

(1) Preparation of the ethyl-esterified tea oil: the tea seed oil and ethanol were mixed at a volume ratio of 1:3 to obtain a mixture, and the immobilized lipase of Lipozyme TL IM that was 2.5% by mass of the tea seed oil was added to the mixture, and then the above mixed materials reacted at 50° C. for 15 h; centrifugation was performed at 4000 rpm for 25 min, and then the supernatant was rinsed with a saturated sodium chloride aqueous solution 2.5 times as much as the mass of the tea seed oil; then the rinsed supernatant was allowed to stand layering, and the lower layer was removed to obtain the ethyl-esterified tea oil; and (2) evenly mixing the ethyl-esterified tea oil, the oregano oil, the *melaleuca alternifolia* oil, the pumpkin seed oil, the prickly pear seed oil, the passion fruit seed oil, and the nano germanium oxide, so as to obtain the tea massage oil.

The massage oil prepared in this example has a density of 0.940 g/mL and a viscosity of 34 mPa·s, which are only ¼ of the corresponding values of the general vegetable oil; therefore, it is easy to disperse, good in bacteriostatic performance, and stable, having no obvious change after being sealed at room temperature for 18 months.

EXAMPLE 7

Effect Evaluation

Determination of the application effects of the tea massage oils prepared in Examples 1-6:

Experimental methods: 60 male volunteers were divided into 6 groups. They used the tea massage oils prepared in Examples 1-6 for 30 days, respectively, and got their comfort (≤25 points), fatigue elimination (≤25 points), scar reduction (≤25 points), and skin vitality (≤25 points) scored.

The experimental results are shown in Table 1. The results showed that the tea massage oils prepared in Examples 1-6 were superior in application effects to the tea massage oils commercially available in the domestic market.

TABLE 1

Evaluation of application effects of the tea massage oils prepared in Examples 1-6 ($\bar{x} \pm SD$, n = 10)

| Sample | Effect score |
| --- | --- |
| Example 1 | 94 ± 6 |
| Example 2 | 93 ± 5 |
| Example 3 | 90 ± 7 |
| Example 4 | 89 ± 8 |
| Example 5 | 91 ± 6 |
| Example 6 | 92 ± 7 |
| Domestic tea massage oil | 65 ± 8 |

The above examples are preferred embodiments of the present invention, but the embodiments of the present invention are not limited thereto, and any other alterations, modifications, substitutions, combinations and simplifications made without departing from the spirit and principle of the present invention should all be equivalent replacements and included in the scope of protection of the present invention.

The invention claimed is:

1. A tea massage oil comprising:
40-87% ethyl-esterified tea oil,
5-15% oregano oil,
2-12% *melaleuca alternifolia* oil,
2-10% pumpkin seed oil,
2-10% prickly pear seed oil,
1-10% passion fruit seed oil, and
1-5% nano germanium oxide.

2. The tea massage oil of claim 1 comprising;
70% ethyl-esterified tea oil,
10% oregano oil,
5% *melaleuca alternifolia* oil,
5% pumpkin seed oil,
5% prickly pear seed oil,
3% passion fruit seed oil, and
2% nano germanium oxide.

3. A method for improving the efficacy of a massage treatment for fatigue-relief, improving men's health, and/or scare-removal, and/or skin-activation comprising, applying to a subject in need thereof the tea massage oil according to claim 1, thereby improving the efficacy of the massage treatment.

4. A method for preparing the tea massage oil according to claim 1, comprising the following steps: evenly mixing the ethyl-esterified tea oil, the oregano oil, the *melaleuca alternifolia* oil, the pumpkin seed oil, the prickly pear seed oil, the passion fruit seed oil, and the nano germanium oxide, so as to obtain the tea massage oil, wherein the ethyl-esterified tea oil is prepared according to the process comprising: mixing tea seed oil with ethanol to obtain a mixture, adding an immobilized lipase to the mixture; centrifuging the mixture, removing and rinsing resulting supernatant with a saturated sodium chloride aqueous solution; allowing the rinsed supernatant to stand for a sufficient duration to produce an upper and lower layer, and removing the lower layer to obtain the ethyl-esterified tea oil.

5. The method of claim 4 wherein the volume ratio of the tea seed oil to ethanol is 1:(1 to 5), the amount of the immobilized lipase is 0.5% to 5% of the mass of the tea seed oil, the reaction temperature is 30° C. to 70° C., and the reaction time is 12-24 h.

6. The method of claim 4, wherein the immobilized lipase is one or both of a lipase immobilized on a hydrophobic carrier (acrylic resin) and/or a lipase immobilized on a non-compressible silica gel carrier.

7. The method of claim 4 wherein the centrifugal speed is 1000-5000 rpm, and the centrifugal time is 20-60 min; and the amount of the saturated sodium chloride aqueous solution is 0.5 to 3 times the mass of the tea seed oil.

* * * * *